United States Patent [19]
Kao et al.

[11] Patent Number: 5,661,024
[45] Date of Patent: Aug. 26, 1997

[54] DNA ENCODING A HUMAN SEROTONIC (5-HT$_2$) RECEPTOR AND USES THEREOF

[75] Inventors: Hung-Teh Kao, Hackensack; Paul R. Hartig, Mahwah; Theresa Branchek, Teaneck, all of N.J.

[73] Assignee: Synaptic Pharmaceutical Corporation, Paramus, N.J.

[21] Appl. No.: 347,591

[22] Filed: Nov. 30, 1994

Related U.S. Application Data

[63] Continuation of Ser. No. 232,325, Apr. 25, 1994, abandoned, which is a continuation of Ser. No. 999,661, Dec. 29, 1992, abandoned, which is a continuation of Ser. No. 635,402, Dec. 31, 1990, abandoned, which is a continuation of Ser. No. 429,832, Oct. 31, 1989, abandoned.

[51] Int. Cl.$^6$ .............................. C12N 5/00; C12N 7/00; C12N 15/00; C07H 21/02
[52] U.S. Cl. .................... 435/240.2; 435/235.1; 435/325; 435/357; 435/361; 435/367; 536/23.5; 935/70
[58] Field of Search ................... 435/69.1, 70.5, 435/71.1, 172.1, 240.2, 252.3, 320.1, 235.1; 536/23.5; 935/69, 70, 72, 73

[56] References Cited

U.S. PATENT DOCUMENTS

| | | | |
|---|---|---|---|
| 4,985,352 | 1/1991 | Julius et al. | 935/77 |
| 5,155,218 | 10/1992 | Weinshank et al. | |
| 5,360,735 | 11/1994 | Weinshank et al. | |

OTHER PUBLICATIONS

Stevens (1987), Nature, vol. 328, pp. 198–199.
Kramer et al. "Regulated expression of human interferon in yeast," *PNAS*, vol. 81, 1984, pp. 367–370.
R. J. Kaufman, "High Level Production of Proteins in Mammalian Cells," in *Genetic Engineering*, ed. J. Setlow (Plenum Press, NY) 1987, pp. 155–198.
T. J. Harris, "Expression of Eukaryotic Genes in *E. Coli*," in *Genetic Engineering*, ed R. Williamson (Academic Press, NY) 1983, pp. 127–141.
Fargin et al. "Genomic Clone G-21 Which Resembles BAR Encodes 5-HT1A," *Nature*, vol. 335, Sep. 1988, pp. 358–360.
Pritchett et al. "Structure and Function of Rat 5HT2 Receptor," *EMBO J*, vol. 7, Dec. 1988, pp. 4135–4140.
Julius et al. "Molecular characterization of serotonin 1c receptor," *Science*, vol. 241, Jul. 1988, pp. 558–564.
Hoyer et al. "Serotonin Receptors in the Human Brain," *Brain Research*, vol. 376, 1986, pp. 97–107.
Lyon, R.A., et al. Molecular Pharmacology 1986; 31:194–199 (Exhibit D).
Julius, D. et al. Neurobiology 1990; 87:928–932 (Exhibit E).

*Primary Examiner*—Debra Brittingham
*Attorney, Agent, or Firm*—John P. White

[57] ABSTRACT

The present invention provides an isolated nucleic acid molecule encoding an 5-HT$_2$ receptor, and an isolated protein which is a human 5-HT$_2$ receptor.

The invention also provides vectors comprising DNA molecules encoding a human 5-HT$_2$ receptor, and vectors adapted for expression of the 5-HT$_2$ receptor in bacterial, yeast, or mammalian cells.

In addition, the invention provides a DNA probe useful for detecting nucleic acid encoding the 5-HT$_2$ receptor, a method for determining whether a ligand which is not known to be capable of binding to the 5-HT$_2$ receptor can bind to the 5-HT$_2$ receptor, a method for detecting the presence of 5-HT$_2$ receptor on the surface of a cell, and a method of screening drugs to identify drugs which specifically interact with, and bind to, the 5-HT$_2$ receptor.

The invention herein also concerns an antibody directed to the human 5-HT$_2$ receptor, such as a monoclonal antibody directed to an epitope of the 5-HT$_2$ receptor present on the surface of a cell and having an amino acid sequence included within the amino acid sequence shown in FIG. 2.

18 Claims, 11 Drawing Sheets

FIGURE 2A

```
Met Asp Ile Leu Cys Glu Glu Asn Thr Ser
A T G G A T A T T C T T T G T G A A G A A A A T A C T T C T
            10                  20                  30

Leu Ser Ser Thr Thr Asn Ser Leu Met Gln
T T G A G C T C A A C T A C G A A C T C C T A A T G C A A
            40                  50                  60

Leu Asn Asp Asp Thr Arg Leu Tyr Ser Asn
T T A A A T G A T G A C A C C A G G C T C T A C A G T A A T
            70                  80                  90

Asp Phe Asn Ser Gly Glu Ala Asn Thr Ser
G A C T T T A A C T C C G G A G A A G C T A A C A C T T C T
            100                 110                 120

Asp Ala Phe Asn Trp Thr Val Asp Ser Glu
G A T G C A T T T A A C T G G A C A G T C G A C T C T G A A
            130                 140                 150

Asn Arg Thr Asn Leu Ser Cys Glu Gly Cys
A A T C G A A C C A A C C T T T C C T G T G A A G G G T G C
            160                 170                 180
```

FIGURE 2B

```
      Leu   Ser   Pro   Ser   Cys   Leu   Ser   Leu   Leu   His
      C T C T C A C C G T C G T G T C T C C T T A C T T C A T
              190                 200                 210

Leu   Gln   Glu   Lys   Asn   Trp   Ser   Ala   Leu   Leu
      C T C C A G G A A A A A A C T G G T C T G C T T T A C T G
              220                 230                 240

Thr   Ala   Val   Val   Ile   Ile   Leu   Thr   Ile   Ala
      A C A G C C G T A G T G A T T A T T C T A A C T A T T G C T
              250                 260                 270

Gly   Asn   Ile   Leu   Val   Ile   Met   Ala   Val   Ser
      G G A A A C A T A C T C G T C A T C A T G G C A G T G T C C
              280                 290                 300

Leu   Glu   Lys   Lys   Leu   Gln   Asn   Ala   Thr   Asn
      C T A G A G A A A A A G C T G C A G A A T G C C A C C A A C
              310                 320                 330

Tyr   Phe   Leu   Met   Ser   Leu   Ala   Ile   Ala   Asp
      T A T T T C C T G A T G T C A C T T G C C A T A G C T G A T
              340                 350                 360

Met   Leu   Leu   Gly   Phe   Leu   Val   Met   Pro   Val
      A T G C T G C T G G G T T T C C T T G T C A T G C C C G T G
              370                 380                 390

Ser   Met   Leu   Thr   Ile   Leu   Tyr   Gly   Tyr   Arg
      T C C A T G T T A A C C A T C C T G T A T G G G T A C C G G
              400                 410                 420
```

FIGURE 2C

```
Trp  Pro  Leu  Pro  Ser  Lys  Leu  Cys  Ala  Val
T G G C C T C T G C C G A G C A A G C T T T G T G C A G T C
          430              440              450

Trp  Ile  Tyr  Leu  Asp  Val  Leu  Phe  Ser  Thr
T G G A T T T A C C T G G A C G T G C T C T T C T C C A C G
          460              470              480

Ala  Ser  Ile  Met  His  Leu  Cys  Ala  Ile  Ser
G C C T C C A T C A T G C A C C T C T G C G C C A T C T C G
          490              500              510

Leu  Asp  Arg  Tyr  Val  Ala  Ile  Gln  Asn  Pro
C T G G A C C G C T A C G T C G C C A T C C A G A A T C C C
          520              530              540

Ile  His  His  Ser  Arg  Phe  Asn  Ser  Arg  Thr
A T C C A C C A C A G C C G C T T C A A C T C C A G A A C T
          550              560              570

Lys  Ala  Phe  Leu  Lys  Ile  Ile  Ala  Val  Trp
A A G G C A T T T C T G A A A A T C A T T G C T G T T T G G
          580              590              600

Thr  Ile  Ser  Val  Gly  Ile  Ser  Met  Pro  Ile
A C C A T A T C A G T A G G T A T A T C C A T G C C A A T A
          610              620              630

Pro  Val  Phe  Gly  Leu  Gln  Asp  Asp  Ser  Lys
C C A G T C T T T G G G C T A C A G G A C G A T T C G A A G
          640              650              660
```

FIGURE 2D

```
Val Phe Lys Glu Gly Ser Cys Leu Leu Ala
G T C T T T A A G G A G G G G A G T T G C T T A C T T G C C
          670                 680                 690

Asp Asp Asn Phe Val Leu Ile Gly Ser Phe
G A T G A T A A C T T T G T C C T G A T C G G C T C T T T T
          700                 710                 720

Val Ser Phe Phe Ile Pro Leu Thr Ile Met
G T G T C A T T T T T C A T T C C C T T A A C C A T C A T G
          730                 740                 750

Val Ile Thr Tyr Phe Leu Thr Ile Lys Ser
G T G A T C A C C T A C T T T C T A A C T A T C A A G T C A
          760                 770                 780

Leu Gln Lys Glu Ala Thr Leu Cys Val Ser
C T C C A G A A A G A A G C T A C T T T G T G T G T A A G T
          790                 800                 810

Asp Leu Gly Thr Arg Ala Lys Leu Ala Ser
G A T C T T G G C A C A C G G G C C A A A T T A G C T T C T
          820                 830                 840

Phe Ser Phe Leu Pro Gln Ser Ser Leu Ser
T T C A G C T T C C T C C C T C A G A G T T C T T T G T C T
          850                 860                 870

Ser Glu Lys Leu Phe Gln Arg Ser Ile His
T C A G A A A A G C T C T T C C A G C G G T C G A T C C A T
          880                 890                 900
```

FIGURE 2E

```
Arg Glu Pro Gly Ser Tyr Thr Gly Arg Arg
A G G A G C C A G G G T C C T A C A G G C A G G A G G
        910             920             930

Thr Met Gln Ser Ile Ser Asn Glu Gln Lys
A C T A T G C A G T C C A T C A G C A A T G A G C A A A A G
        940             950             960

Ala Cys Lys Val Leu Gly Ile Val Phe Phe
G C A T G C A A G G T G C T G G G C A T C G T C T T C T T C
        970             980             990

Leu Phe Val Val Met Trp Cys Pro Phe Phe
C T G T T T G T G G T G A T G T G G T G C C C T T T C T T C
       1000            1010            1020

Ile Thr Asn Ile Met Ala Val Ile Cys Lys
A T C A C A A A C A T C A T G G C C G T C A T C T G C A A A
       1030            1040            1050

Glu Ser Cys Asn Glu Asp Val Ile Gly Ala
G A G T C C T G C A A T G A G G A T G T C A T T G G G G C C
       1060            1070            1080

Leu Leu Asn Val Phe Val Trp Ile Gly Tyr
C T G C T C A A T G T G T T T G T T T G G A T C G G T T A T
       1090            1100            1110

Leu Ser Ser Ala Val Asn Pro Leu Val Tyr
C T C T C T T C A G C A G T C A A C C C A C T A G T C T A C
       1120            1130            1140
```

FIGURE 2F

```
Thr   Leu   Phe   Asn   Lys   Thr   Tyr   Arg   Ser   Ala
A C A C T G T T C A A C A A G A C C T A T A G G T C A G C C
      1150              1160              1170

Phe   Ser   Arg   Tyr   Ile   Gln   Cys   Gln   Tyr   Lys
T T T T C A C G G T A T A T T C A G T G T C A G T A C A A G
      1180              1190              1200

Glu   Asn   Lys   Lys   Pro   Leu   Gln   Leu   Ile   Leu
G A A A C A A A A A A C C A T T G C A G T T A A T T T T A
      1210              1220              1230

Val   Asn   Thr   Ile   Pro   Ala   Leu   Ala   Tyr   Lys
G T G A A C A C A A T A C C G G C T T T G G C C T A C A A G
      1240              1250              1260

Ser   Ser   Gln   Leu   Gln   Met   Gly   Gln   Lys   Lys
T C T A G C C A A C T T C A A A T G G G A C A A A A A A A G
      1270              1280              1290

Asn   Ser   Lys   Gln   Asp   Ala   Lys   Thr   Thr   Asp
A A T T C A A A G C A A G A T G C C A A G A C A A C A G A T
      1300              1310              1320

Asn   Asp   Cys   Ser   Met   Val   Ala   Leu   Gly   Lys
A A T G A C T G C T C A A T G G T T G C T C T A G G A A A G
      1330              1340              1350

Gln   His   Ser   Glu   Glu   Ala   Ser   Lys   Asp   Asn
C A G C A T T C T G A A G A G G C T T C T A A A G A C A A T
      1360              1370              1380
```

FIGURE 2G

| Ser | Asp | Gly | Val | Asn | Glu | Lys | Val | Ser | Cys |
|---|---|---|---|---|---|---|---|---|---|
| A G C | A C G | G A G | T G A | A T G | A A A | A G G | T G A | G C T | G T |

1390                     1400                     1410

| Val | *** | *** | Ala | Ser | Cys | Arg | Gly | Asn | Cys |
|---|---|---|---|---|---|---|---|---|---|
| G T G | T G A | T A G | G C T | A G T | T G C | C G T | G G C | A A C | T G T |

1420                     1430                     1440

G G A A G G C A C A C T G A G C A A G T T T T C A C C T A T
        1450                     1460                     1470

C T G G T T T T T T T T G
        1480

Rat Serotinin 5-HT₂ Receptor

- Leucine zipper
- Differ in human 5-HT₂ receptor sequence

DNA ENCODING A HUMAN SEROTONIC (5-HT$_2$) RECEPTOR AND USES THEREOF

This application is a continuation of U.S. Ser. No. 08/232,325, filed Apr. 25, 1994, now abandoned, which is a continuation of U.S. Ser. No. 07/999,661, filed Dec. 29, 1992, now abandoned, which is a continuation of U.S. Ser. No. 635,402, filed Dec. 31, 1990, now abandoned, which is a continuation of U.S. Ser. No. 429,832, filed Oct. 31, 1989, now abandoned.

BACKGROUND OF THE INVENTION

Throughout this application various publications are referenced by full citations within parentheses. The disclosures of these publications in their entireties are hereby incorporated by reference in this application in order to more fully describe the state of the art to which this invention pertains.

Pharmacological studies, and more recently gene cloning, have established that multiple receptor subtypes exist for most, if not all, neurotransmitters. The existence of multiple receptor subtypes provides one mechanism by which a single neurotransmitter can elicit distinct cellular responses.

The variation in cellular response can be achieved by the association of individual receptor subtypes with different G proteins and different signalling systems. Further flexibility is provided by the ability of distinct receptors for the same ligand to activate or inhibit the same second messenger system.

Individual receptor subtypes reveal characteristic differences in their abilities to bind a number of ligands, but the structural basis for the distinct ligand-binding properties is not known. Physiologists and pharmacologists have attempted to specify particular biological functions or anatomical locations for some receptor subtypes, but this has met with limited success. Similarly, the biochemical mechanisms by which these receptors transduce signals across the cell surface have been difficult to ascertain without having well-defined cell populations which express exclusively one receptor subtype.

Receptors for serotonin (5-hydroxytryptamine) are termed serotonin or 5-HT receptors. The 5-HT$_2$ receptor belongs to the family of rhodopsin-like signal transducers which are distinguished by their seven-transmembrane configuration and their functional linkage to G-proteins. While all the receptors of the serotonin type are recognized by serotonin, they are pharmacologically distinct and are encoded by separate genes. These receptors, known as subtypes, are generally coupled to different second messenger pathways that are linked through guanine-nucleotide regulatory (G) proteins. Among the serotonin receptors, 5-HT$_{1A}$, 5-HT$_{1B}$, and 5-HT$_{1D}$ receptors inhibit adenylate cyclase, and 5-HT$_{1C}$ and 5-HT$_2$ receptors activate phospholipase C pathways, stimulating breakdown of polyphosphoinositides.

Radioligand filtration binding techniques have been employed to characterize the serotonin receptor family (Schmidt and Peroutka, FASEB J. 3:2242 (1989)). Using these methods, at least two classes of G-protein coupled serotonin receptors have been described, 5-HT1, and 5-HT$_2$. These differ in their selectivity for drugs. 5-HT$_1$ receptors display high (nanomolar) affinity for serotonin and can be labeled with [$^3$H] 5-HT. 5-HT$_2$ receptors display low affinity for serotonin but have high (nanomolar) affinity for antagonists such as Ketanserin, Mesulergine, Metergoline and d-LSD. Genes for the 5-HT$_{1A}$ receptor (Fargin, et al., Nature 335:358–360 (1988); Kobilka, et al., Nature 329:75–79 (1987)) and the 5-HT$_{1C}$ receptor (Julius, et al., Science 241:558–564 (1988)) have been isolated.

Applicants have cloned a human 5-HT$_2$ receptor, clone 6B, which has been transfected into a heterologous expression system, producing a membrane protein with binding properties consistent with its preliminary characterization based on amino acid homology as the 5-HT$_2$ receptor subtype. The results from binding studies are consistent with the projected subtype based on amino acid sequence homology.

The receptor encoded by clone 6B shares numerous sequence and structural properties with the family of receptor molecules that has been predicted to span the lipid bilayer seven times. This family includes rhodopsin and related opsins (Nathans, J. and Hogness, D. S., Cell 34:807 (1983)), the α and β adrenergic receptors (Dohlman, H. G., et al., Biochemistry 26:2657 (1987)), the muscarinic cholinergic receptors (Bonner, T. I., et al., Science 237:527 (1987)), the substance K neuropeptide receptor, (Masu, Y., et al., Nature 329:836 (1987)), the yeast mating factor receptors, (Burkholder, A. C. and Hartwell, L. H., Nucl. Acids Res. 13:8463(1985); Hagan, D. C., et al., Proc. Natl. Acad. Sci. USA 83:1418 (1986)); Nakayama, N. et al., EMBO J. 4:2643 (1985)), the serotonin receptor, and the oncogene c-mas, (Young, et al., Cell 45:711 (1986)). Each of these receptors is thought to transduce extracellular signals by interaction with guanine nucleotide-binding (G) proteins (Dohlman, H. G., et al., Biochemistry 26:2657 (1987); Dohlman, H. G., et al., Biochemistry 27:1813 (1988); O'Dowd, B. F., et al., Ann. Rev. Neurosci., in press).

Membranes of cells transfected with clone 6B bind both $^3$H-Ketanserin and $^3$H-DOB, demonstrating that the reported "hallucinogen receptor" must be an affinity state of the 5-HT$_2$ receptor rather than a distinct receptor subtype. Thus, the argument of Titeler (Lyon, et al. Mol. Pharm. 31:194–199 (1987)) for multiple affinity states of the 5-HT$_2$ receptor is supported and that of Peroutka (Pierce, P. A., and S. J. Peroutka J. Neurochem. 52:656–658 (1989)) for multiple 5-HT$_2$ receptor subtypes is not. This observation provides the opportunity to use the transfected human 5-HT$_2$ receptor as a tool for the development of drugs which induce or which interfere with hallucinogenesis, caused either by disease processes or by drugs of abuse.

Strader, Sigal and Dixon recently published a model for the neurotransmitter binding site of G protein-coupled receptors (FASEB J. 3: 1825–1832 (1989)). According to this model, adrenergic receptors contain two serine residues in transmembrane segment V (TM5) which hydrogen bond to the catechol ring hydroxyl groups of adrenergic agonists. Serotonergic receptors, which must bind agonist ligands containing a single ring hydroxyl group, are distinguished by a the presence of a single serine residue in this region of TM5. The rat serotonin 5-HT$_2$ receptor sequence (Pritchett, et al., EMBO J. 17: 4135–4140 (1988)) shows a single serine residue in this region of TM5, as expected. Surprisingly, the human 5-HT$_2$ receptor sequence shown in FIG. 2 violates this model by exhibiting two serine residues in this region, as would be expected for an adrenergic receptor. This raises the interesting possibility that the human 5-HT$_2$ receptor may have evolved the possibility of interacting with epinephrine, norepinephrine and adrenergic antagonists, in addition to its known interactions with serotonergic drugs. This possible acquisition by the human 5-HT$_2$ receptor of a neurotransmitter cross-reactivity may have functional consequences in the normal or diseased human brain. We hypothesize that the human 5-HT$_2$ receptor may have evolved the capacity to interact with two separate neurotransmitter systems, the serotonergic and adrenergic systems. Since both systems are widely distributed in the brain and both may act in a neuromodulatory fashion to activate receptors far from the neurotransmitter release site, it is conceivable that the human 5-$HT_2$ receptor may be activated by a wide array of both serotonergic and adrenergic nerve terminals. In that case, classical adrenergic and serotonergic brain or peripheral nervous system functions may be mediated in part by this single receptor site. Thus, it may be possible to modulate serotonergic functions by administration of adrenergic drugs and to modulate adrenergic functions by administration of serotonergic drugs. These possibilities are currently under investigation in a variety of adrenergic and serotonergic binding, second messenger and physiological response assays.

Another interesting feature of the human 5-$HT_2$ receptor is the presence of a leucine zipper motif in transmembrane segment I (FIGS. 3A–3B). This motif, consisting of four or more leucine residues repeated every seventh amino acid residue of an alpha-helix, has been implicated as the site of protein—protein interactions in dimerizing, or multisubunit proteins (McCormack et al. Nature 340: 103 (1989)). The presence of this motif in the human 5-$HT_2$ receptor suggests that this receptor may dimerize in the membrane or may interact with other unidentified proteins (or with G proteins) via the leucine zipper of transmembrane segment I. This may have significant implications for the function of the human 5-$HT_2$ receptor. In addition, it may be possible to design drugs which interfere with the leucine zipper region of the 5-$HT_2$ receptor, thus modulating the functional activity of this serotonergic response system.

SUMMARY OF THE INVENTION

The present invention provides an isolated nucleic acid molecule encoding a human 5-$HT_2$ receptor.

This invention also provides an isolated protein which is a human 5-$HT_2$ receptor.

The invention also provides vectors comprising DNA molecules encoding a human 5-$HT_2$ receptor, for example a plasmid comprising the DNA encoding the 5-$HT_2$ receptor, designated clone 6B.

Additionally, the present invention provides vectors adapted for expression in bacterial, yeast, or mammalian cells which comprise a DNA molecule encoding the 5-$HT_2$ receptor and the regulatory elements necessary for expression of the DNA in the cell.

The present invention further provides the transfected Ltk⁻ cell designated L-NGC-5$HT_2$ and deposited under ATCC Accession No. CRL 10287.

In addition, the invention provides a DNA probe useful for detecting nucleic acid encoding the 5-$HT_2$ receptor comprising a nucleic acid molecule of at least about 15 nucleotides having a sequence complementary to a sequence included within the sequence shown in FIGS. 2A–2G.

This invention also provides a method for determining whether a ligand which is not known to be capable of binding to the 5-$HT_2$ receptor can bind to the 5-$HT_2$ receptor.

This invention also concerns an antibody directed to the human 5-$HT_2$ receptor.

This invention additionally concerns a monoclonal antibody directed to an epitope of the 5-$HT_2$ receptor present on the surface of a cell and having an amino acid sequence included within the amino acid sequence shown in FIGS. 2A–2G.

This invention concerns a method for detecting the presence of 5-$HT_2$ receptor on the surface of a cell.

This invention also concerns a method of screening drugs to identify drugs which specifically interact with, and bind to, the 5-$HT_2$ receptor.

The bold region represents the human 5-$HT_2$ coding sequence. Restriction sites are indicated.

FIGS. 2A–2G. Nucleotide Sequence and Deduced Amino Acid Sequence of the Human 5-$HT_2$ Receptor.

Numbers indicate nucleotide position. DNA sequence of cDNA clone 6B was determined by the chain termination method of Sanger, et al., on denatured double-stranded plasmid templates (Chen and Seeburg, DNA 4:165,1985) using Sequenase. Deduced amino acid sequence by translation of a long open reading frame is shown.

Figure 1:
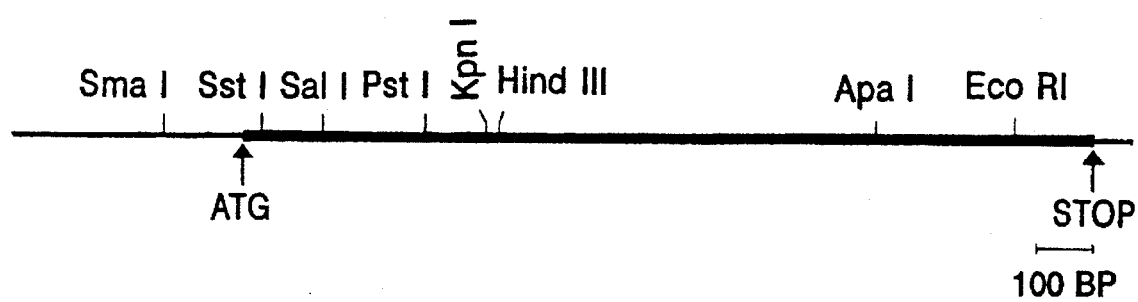
FIG. 1. Restriction Map of Clone.
Figure 3A:
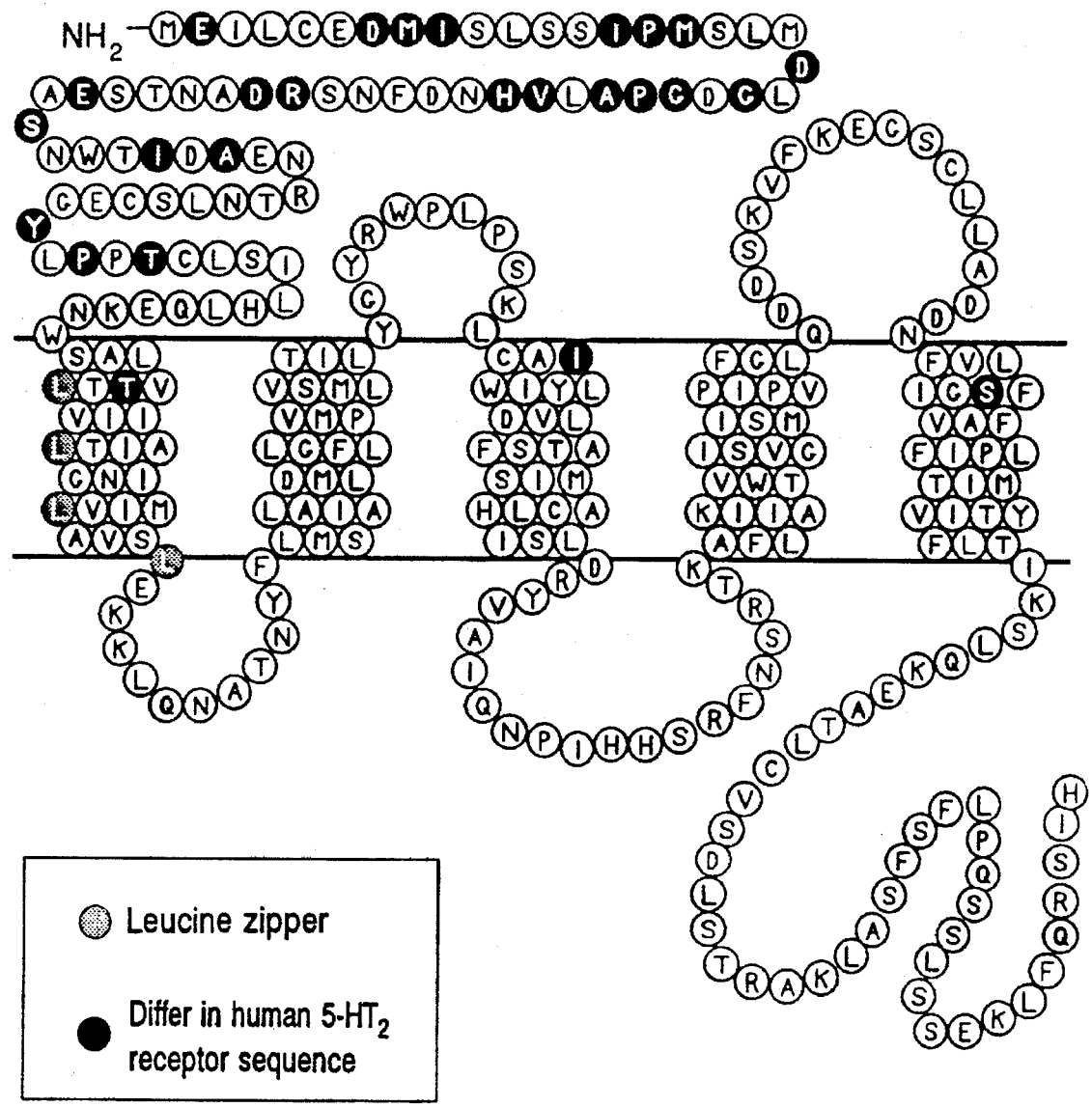
Figure 3B:
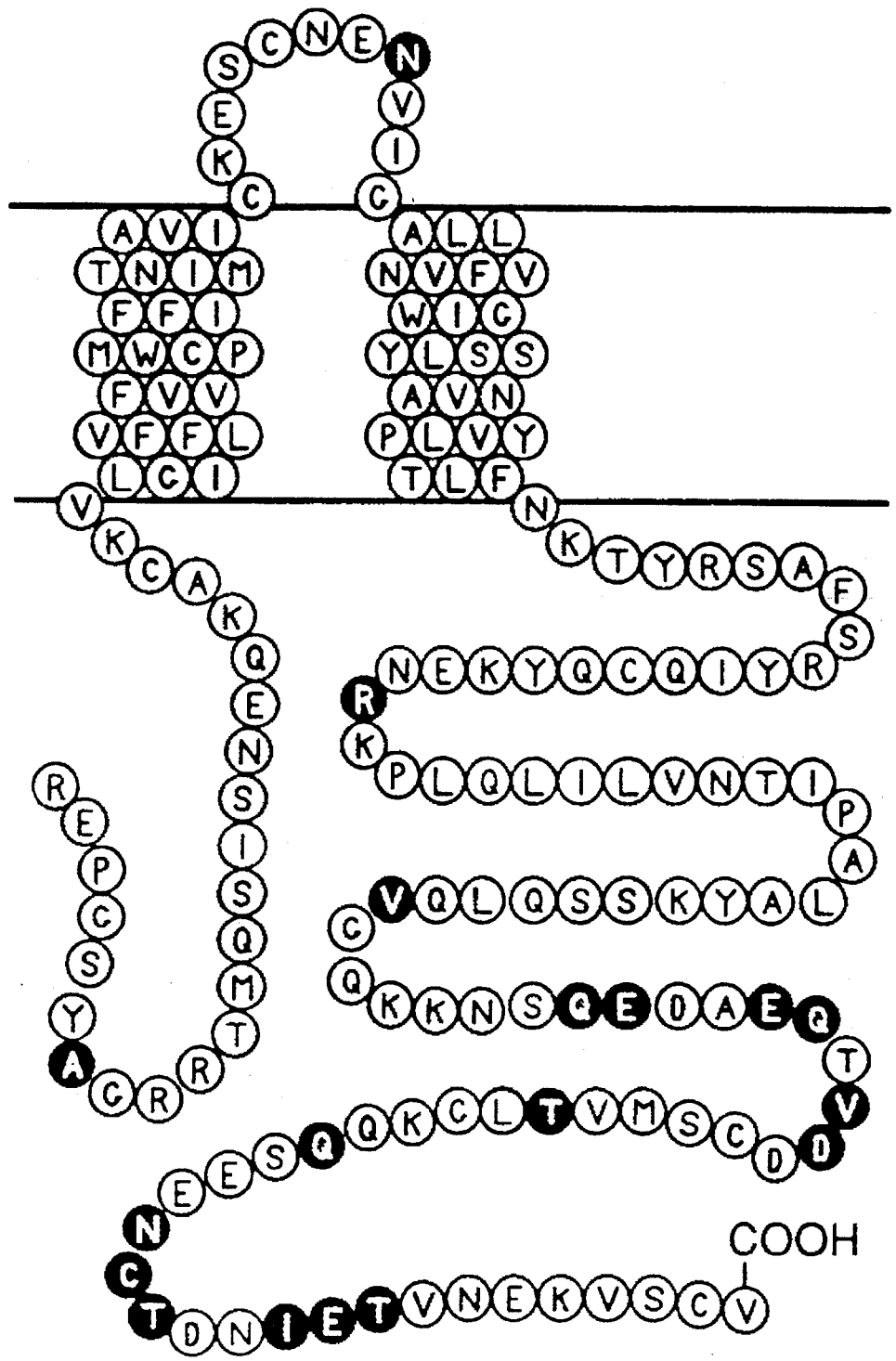

FIGS. 3A–3B. Comparison of the Sequence Between the Rat and Human 5-$HT_2$ Receptors.

The amino acid sequence (single letter code) of the rat 5-$HT_2$ receptor pictured as a protein with the putative transmembrane domains traversing the membrane seven times. Filled in circles represent residues of the rat receptor that differ from corresponding residues in the same locations in the sequence of the human receptor.

Figure 4:
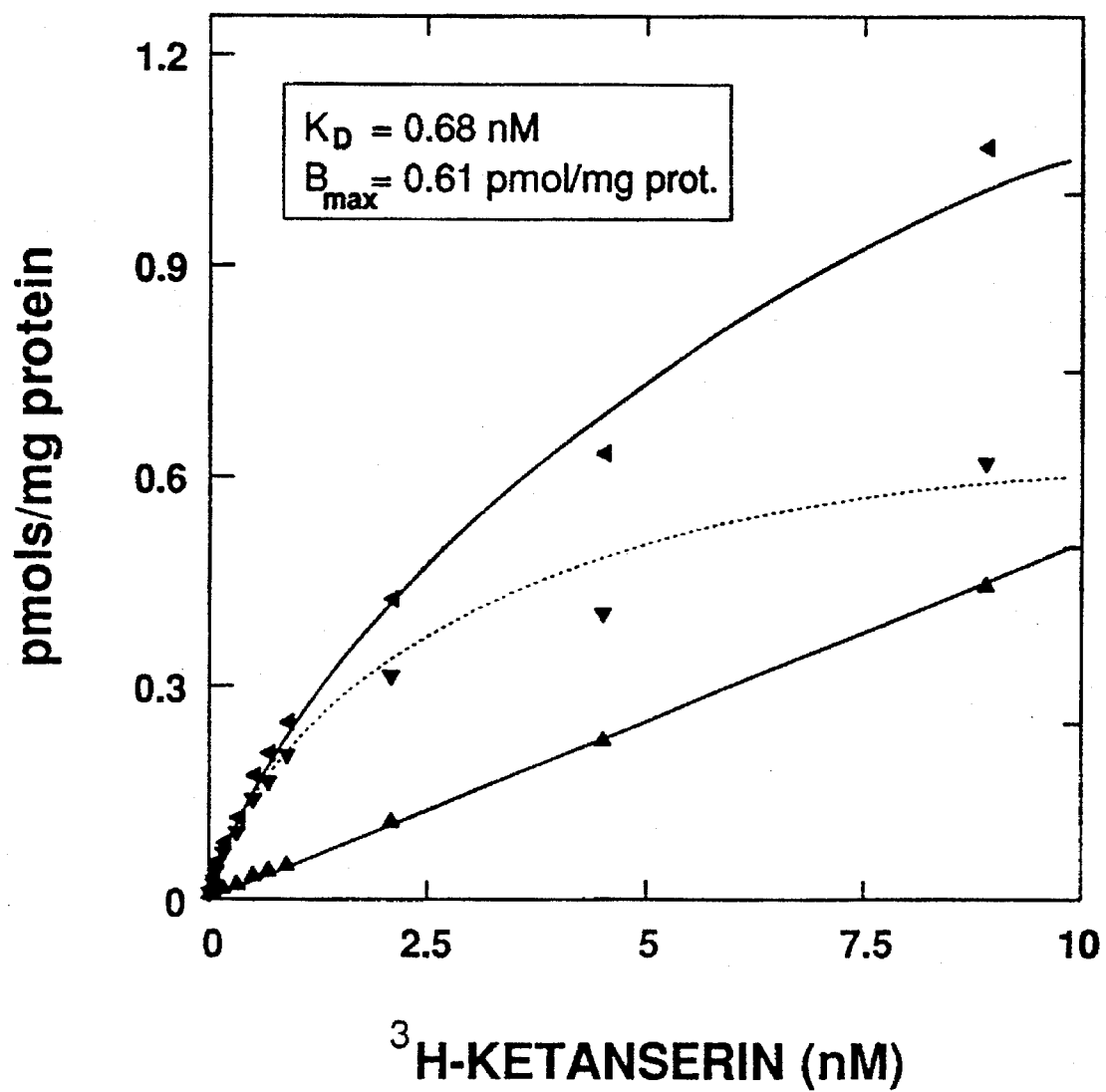

FIG. 4. Saturation Curves for the Binding of ³H-Ketanserin to Stably Transfected Ltk⁻ Cells.

The lower curve represents non-specific binding as defined by $10^{-6}M$ Mianserin. The middle curve is the calculated specific binding. For this experiment, $K_D$=0.678 nM; $B_{max}$=0.602 pmole/mg protein. This dissociation constant is consistent with the designation of 6B as a 5-$HT_2$ receptor.

DETAILED DESCRIPTION OF THE INVENTION

This invention provides an isolated nucleic acid molecule encoding a human 5-$HT_2$ receptor, for example a DNA molecule or a cDNA molecule.

This invention provides DNA encoding a 5-$HT_2$ receptor, for example the genomic DNA or cDNA having a coding sequence substantially the same as the coding sequence shown in FIGS. 2A–2G.

This invention provides an isolated protein which is a human 5-$HT_2$ receptor. An example of such a protein has substantially the same amino acid sequence as the amino acid sequence shown in FIGS. 2A–2G. A means for obtaining isolated human 5-$HT_2$ receptor is expressing DNA encoding the receptor in a suitable host, such as a bacterial, yeast, or mammalian cell, using methods well known in the art, and recovering the 5-$HT_2$ receptor after it has been expressed in such a host, again using methods well known in the art.

This invention provides vectors comprising DNA encoding a human 5-$HT_2$ receptor, and DNA and cDNA having a coding sequence substantially the same as the coding sequence shown in FIGS. 2A–2G. Some examples are a plasmid, such as pUC18, or a virus, or a bacteriophage such as lambda bacteriophage.

One example of a plasmid comprising DNA having a coding sequence substantially the same as the coding sequence shown in FIGS. 2A–2G is plasmid designated clone 6B.

This invention further provides a plasmid adapted for expression in a bacterial, yeast, or mammalian cell which comprises DNA encoding the 5-HT$_2$ receptor, or DNA or cDNA having a coding sequence substantially the same as the coding sequence shown in FIGS. 2A–2G, and the regulatory elements necessary to express such DNA in the bacterial, yeast, or mammalian cell. As regards the latter, those skilled in the art will readily appreciate that numerous plasmids may be constructed utilizing existing plasmids and adapted as appropriate to contain the regulatory elements necessary to express the DNA in the mammalian cell. Numerous mammalian cells may be used including, for example, the mouse fibroblast cell NIH3T3, CHO cells, HeLa cells, etc. One example of a plasmid adapted for the expression of a cDNA molecule having a coding sequence substantially the same as the coding sequence shown in FIGS. 2 is the plasmid designated pMO5-6B described more fully hereinafter and deposited with the American Type Culture Collection under ATCC Accession No. 40696.

This deposit and the other deposit discussed herein were made pursuant to, and in satisfaction of, the Budapest Treaty on the International Recognition of the Deposit of Microorganisms for the Purpose of Patent Procedure and were made with the American Type Culture Collection, 12301 Parklawn Drive, Rockville, Md. 20852.

This invention provides expression plasmids used to transfect mammalian cells, for example Ltk$^-$ cells, comprising plasmids adapted for expression in mammalian cells which comprise DNA encoding a human 5-HT$_2$ receptor, or comprising DNA or cDNA having a coding sequence substantially the same as the coding sequence shown in FIGS. 2A–2G. In one presently preferred embodiment this invention provides an Ltk$^-$ cell transfected with the plasmid designated pMO5-6B. This cell line is designated L-NGC-5HT$_2$ and is deposited under ATCC Accession No. CRL 10287. DNA encoding the 5-HT$_2$ receptor may be otherwise introduced into mammalian cells, e.g., by microinjection, to obtain mammalian cells which comprise DNA, e.g., cDNA or a plasmid, encoding the 5-HT$_2$ receptor.

This invention further provides a method for determining whether a ligand, such as a known or putative drug, which is not known to be capable of binding to the 5-HT$_2$ receptor, can bind to the 5-HT$_2$ receptor. This method comprises contacting a mammalian cell expressing 5-HT$_2$ receptor the with the ligand under conditions permitting binding of ligands known to bind to the 5-HT$_2$ receptor, detecting the presence of any of the ligand bound to the 5-HT$_2$ receptor and thereby determining whether the ligand binds to the 5-HT$_2$ receptor. An example of such a mammalian cell is a mammalian cell comprising a plasmid which comprises a DNA molecule encoding a human 5-HT$_2$ receptor, or DNA or cDNA molecules having coding sequences substantially the same as the coding sequence shown in FIGS. 2A. Another example of such a mammalian cell is an Ltk$^-$ cell comprising a plasmid which comprises a DNA molecule encoding a human 5-HT$_2$ receptor, or DNA or cDNA molecules having coding sequences substantially the same as the coding sequence shown in FIGS. 2A–2G.

This invention still further provides a method of detecting the presence of mRNA coding for the 5-HT$_2$ receptor in a cell which comprises obtaining total mRNA from the cell, using well known methods, and contacting the mRNA so obtained with the cDNA having a coding sequence substantially the same as the coding sequence encoding the 5-HT$_2$ receptor shown in FIGS. 2A–2G, under hybridizing conditions, detecting the presence of mRNA hybridized to the cDNA, and thereby detecting the presence of mRNA coding for the 5-HT$_2$ receptor by the cell.

This invention also provides a DNA probe useful for detecting in a sample nucleic acid encoding the 5-HT$_2$ receptor. Such a probe comprises a nucleic acid molecule of at least about 15 nucleotides having a sequence complementary to a sequence included within the sequence shown in FIGS. 2A–2G. Such nucleic acid probe technology is well known to those skilled in the art who will readily appreciate that such probes may vary greatly in length and may be labeled with a detectable label, such as a radioisotope or fluorescent dye, to facilitate detection of the probe.

This invention provides an antibody directed to the human 5-HT$_2$ receptor. Such an antibody may be serum-derived or monoclonal and may be prepared using methods well known in the art. For example, cells such as SR3T3 cells or Ltk$^-$ cells may be used as immunogens to raise such an antibody. Alternatively, synthetic peptides may be prepared using commercially available machines and the amino acid sequence shown in FIGS. 2A–2G. As a still further alternative, DNA, such as a cDNA or a fragment thereof, may be cloned and expressed and the resulting polypeptide recovered and used as an immunogen. One example of such an antibody is a monoclonal antibody directed to an epitope of the 5-HT$_2$ receptor present on the surface of a cell and having an amino acid sequence substantially the same as any part of the amino acid sequence shown in FIGS. 2A–2G.

Still further this invention provides a method of detecting the presence of the 5-HT$_2$ receptor on the surface of a cell which comprises contacting the cell with a monoclonal or serum-based antibody directed to an exposed epitope on the 5-HT$_2$ receptor under conditions permitting binding of the antibody to the 5-HT$_2$ receptor, and detecting the presence of the antibody bound to the cell, and thereby the presence of the 5-HT$_2$ receptor on the surface of the cell. Such a method is useful in determining whether a given cell is defective relative to the expression of 5-HT$_2$ receptor on the surface of the cell.

Finally, this invention provides a method of screening drugs to identify drugs which specifically interact with, and bind to, the 5-HT$_2$ receptor on the surface of a cell. This method comprises contacting a mammalian cell which is expressing 5-HT$_2$ receptor with a plurality of drugs, known or putative, determining those drugs which bind to the mammalian cell, and thereby identifying drugs which specifically interact with, and bind to, the 5-HT$_2$ receptor. An example of a mammalian cell is the mammalian cell comprising a plasmid which comprises a DNA molecule encoding a human 5-HT$_2$ receptor, or DNA or cDNA molecules having coding sequences substantially the same as the coding sequence shown in FIGS. 2A–2G.

Specifically this invention relates to the first isolation of a human cDNA clone encoding the 5-HT$_2$ receptor and expressing a serotonergic binding site in Ltk$^-$ cells by transfecting the cells with the construct pMO5-6B. A mammalian cell line expressing a human 5-HT$_2$ receptor at the cell surface has been constructed, as determined by pharmacologic methods, thus establishing the first well-defined, cultured cell line with which to study the human 5-HT$_2$ receptor.

The cDNA molecule of the subject invention, which encodes the human 5-HT$_2$ receptor, is useful for obtaining genomic DNA, cDNA or mRNA from human, mammalian or other animal sources, or to isolate related cDNA or genomic clones by the screening of cDNA or genomic libraries. The DNA molecule is obtained by insertion of the whole molecule or fragments thereof into suitable vectors, such as plasmids or bacteriophages, wherein it is replicated and harvested following insertion into suitable bacterial host cells, using methods well known in the art. DNA or RNA fragments derived from the isolated DNA molecule are useful as probes for 'in situ' hybridization or to locate tissues which express this gene, or for other hybridization assays for the presence of the gene or its mRNA in various biological tissues. In addition, synthesized oligonucleotides complementary to the sequence of the DNA molecule are useful as probes for the 5-$HT_2$ receptor gene, for its associated mRNA, or for the isolation of related genes by homology screening of genomic or cDNA libraries, or by the use of amplification techniques such as the Polymerase Chain Reaction.

This invention is also useful to obtain the protein, or fragments of the protein, encoded by the isolated cDNA molecule encoding the human 5-$HT_2$ receptor. Transfecting suitable hosts, such as bacterial, yeast or mammalian cells, with the DNA molecule or fragments thereof in suitable expression vectors such as the plasmid pSVL, using methods well known in the art, yields expression of the 5-$HT_2$ receptor or fragments thereof for direct uses or for experimental study.

Response systems are obtained by coupling the 5-$HT_2$ receptor encoded by the isolated cDNA molecule to an appropriate second messenger response system. These second messenger response systems include, but are not limited to, such systems as phosphoinositide hydrolysis, adenylate cyclase, guanylate cyclase or ion channels. The response system is obtained by transfection of the isolated cDNA molecule into a suitable host cell containing the desired second messenger system. Such a host system is isolated from pre-existing cell lines, or is generated by inserting appropriate components of second messenger systems into existing cell lines. Such a transfection system provides a complete response system for investigation or assay of the activity of the 5-$HT_2$ receptor encoded by the isolated cDNA molecule.

This invention is useful to determine whether a ligand, such as a known or putative drug, is capable of binding to and/or activating the 5-$HT_2$ receptor encoded by the isolated cDNA molecule. Transfection of the isolated cDNA molecule into the cell systems described above provides an assay system for the ability of ligands to bind to and/or to activate the receptor encoded by the isolated DNA molecule. Transfection systems, such as those described above, are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for competitive binding assays. Functional assays of second messenger systems or their sequelae in a transfection system act as assays for binding affinity and efficacy in the the activation of receptor function. Such a transfection system constitutes a "drug discovery system", useful for the identification of natural or synthetic compounds with potential for drug development that can be further modified or used directly as therapeutic compounds to activate or inhibit the natural functions of the 5$HT_2$ receptor encoded by the isolated cDNA molecule. The transfection system is also useful for determining the affinity and efficacy of known drugs at the human 5-$HT_2$ receptor site.

This invention is useful to isolate the genomic DNA encoding the 5-$HT_2$ receptor so that transcriptional regulatory elements from the 5' untranslated region of the isolated gene, and other stability, processing, transcription, translation, and tissue specificity-determining regions from the 3' and 5' untranslated regions of the isolated gene, are made available for further research and application.

This invention is also useful to generate antibodies directed against the 5-$HT_2$ receptor protein encoded by the isolated cDNA molecule. Expression of the protein encoded by the isolated cDNA molecule, in transfection systems such as those described above, provides protein or fragments of protein which are further useful to generate monoclonal or polyclonal antibodies against the isolated receptor, using methods well known in the art. These antibodies are useful to detect the presence of the receptor encoded by the isolated cDNA molecule, or to inhibit the function of the receptor encoded by the isolated cDNA molecule, in living animals, in humans, or in biological tissues or fluids isolated from animals or humans.

This invention identifies an individual receptor subtype protein and tests whether pharmacological compounds interact with it for use in therapeutic treatments. Pharmacological compounds which are directed against specific receptor subtypes will provide effective new therapies with minimal side effects.

In summary, this invention identifies for the first time a human 5-$HT_2$ receptor protein, its amino acid sequence, and its human gene. The information and experimental tools provided by this discovery will be useful to generate new therapeutic agents, and new therapeutic or diagnostic assays for this new receptor protein, its associated mRNA or its associated genomic DNA.

The invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Isolation of a Rat 5-$HT_{1C}$ Receptor cDNA Clone

The rat 5-$HT_{1C}$ gene was isolated as a prerequisite to isolating a clone for the human 5-$HT_2$ gene. This gene was obtained by isolating clones from a rat choroid plexus cDNA library specifically primed with an oligomer complementary to the 3' untranslated region of the rat 5-$HT_{1C}$ receptor. Oligomers complementary to the rat 5-$HT_{1C}$ published sequence (Julius, et al., Science 241: 558–564 (1988) were labeled with $^{32}$P-ATP and T4 Kinase (Maniatis et al, 1982). Clones showing positive hybridization to the probe were picked and inserts subcloned into the sequencing vector pUR250 (Ruther, Nucl. Acids Res 10:5765–5772 (1982)). Sequencing via the Sanger dideoxy method (Sanger, et al., Proc. Natl. Acad. Sci. 74:5463–5467 (1977)) confirmed the isolation of a clone containing the entire coding region of the gene.

Isolation of a Human 5-$HT_2$ Receptor cDNA Clone

Initially, a human brain stem cDNA library provided by Stratagene (La Jolla, Calif.) was screened using a probe made from a rat 5-$HT_{1C}$ receptor gene. This gene had been subcloned into the vector pGem1 (Sma I to Eco RI; Promega-Biotec; Madison, Wis.). Sense strand RNA transcribed by Sp6 polymerase served as a template for the generation of a high specific activity cDNA which was produced by reverse transcription with AMV reverse transcriptase and random primers. The reason for using this particular method was to avoid background problems we have encountered when generating probes using other methods.

Hybridization was performed at 60° C. in a solution containing 5× SSC (1× SSC is 0.15M sodium chloride, 0.015M sodium citrate), 2× Denhardt's (0.02% polyvinylpyrrvolidone, 0.02% Ficoll, and 0.02% bovine serum albumin), 100 mM sodium phosphate pH 8.0, 25 mM EDTA, 0.1% SDS (sodium dodecyl sulfate) and 100 µg/ml of sonicated salmon sperm DNA. The filters were washed at 60° C. in 0.1× SSC containing 0.1% sodium dodecyl sulfate (SDS) and exposed at −70° C. to Kodak XAR film in the presence of an intensifying screen. Lambda phage hybridizing to the probe were plaque purified and plasmid DNA (in the vector pBluescript) self-excised from the lambda vector (lambda ZAP).

One clone (Clone 15) displayed high homology to the published sequence of a rat 5-$HT_2$ receptor clone (Pritchett, et al., EMBO J. 7: 4135–4140 (1988)). However, this clone did not contain the entire coding region and was therefore nonfunctional. Isolation of a Functional Human 5-$HT_2$ Receptor CDNA Clone $^{32}$P-labeled oligomers complementary to the 5' end of Clone 15 were used to probe a human temporal cortex cDNA library (Stratagene, La Jolla, Calif.). Methods for labeling and hybridization are identical to the above. Four independent clones were isolated with the probe, and one, designated 6B, was selected for further studies.

Clone 6B contained the entire coding region for a 5-$HT_2$ receptor and was therefore predicted to be functional. The sequence of this clone is displayed in FIGS. 2A–2G. Clone 6B was subcloned into the mammalian expression vector pMO5 to obtain the construct pMO5-6B.

DNA Sequencing

Nucleotide sequence analysis was done by the Sanger dideoxy nucleotide chain-termination method (Sanger, et al., Proc. Natl. Acad. Sci., 74: 5463–5467, 1977) on denatured double-stranded plasmid templates (Chen and Seeburg, DNA 4: 165, 1985) using Sequenase (U.S. Biochemical Corp., Cleveland, Ohio).

$^3$H-Ketanserin(64.9/mmol;DuPont-NEN, Wilmington, Del.) Binding to Transiently Transfected Cos-7 Cells $^3$H-Ketanserin was used as a radioligand to detect expression of the 5-$HT_2$ gene in transiently transfected Cos-7 cells. Membranes were incubated in 96 well microtiter plates at 37° C. for 15' in solution containing buffer [50 mM Tris Cl, 0.5 mM EDTA, 10 mM $MgSO_4$, 0.1% ascorbate and 10 µM pargyline pH 7.6] 1–2 nM $^3$H-Ketanserin (64.9 Ci/mmol.; DuPont-NEN, Wilmington, Del.), 20–40 µg/0.25 ml protein, and drugs. The total reaction volume was 0.25 ml. The reaction was terminated by filtration through GF/B filters using a Brandel Cell Harvester Model 48R (Brandel, Gaithersburg, Md.). Filters were washed 5×1 sec. with iced buffer to reduce non-specific binding. Dried filters were transferred to scintillation vials and counted by liquid scintillation spectroscopy using a Beckman LS 1701 LSC. Two and one half ml of Formula 963 (Beckman Instruments, Fullerton, Calif.) was used as cocktail. Specific binding was 95% of total binding in transiently transfected cells.

$^3$H-DOB 20.8 Ci/mmole; DuPont-NEN; Wilmington, Del.) Binding to Transiently Transfected Cos-7 Cells Membranes were incubated identically as described for $^3$H-Ketanserin (above). $^3$H-DOB (20.8 Ci/mmol; DuPont-NEN; Wilmington, Del.) was used as a radioligand at a final concentration of 1–2 nM. Specific binding was 70% of total binding in transiently transfected Cos-7 cells.

Saturation Studies

To determine the equilibrium dissociation constant of the 5-$HT_2$ receptor, saturation analysis was performed using $^3$H-Ketanserin as a radioligand. The concentration of the $^3$H-Ketanserin covered a range between 0.25 and 20 nM. Mianserin at 1.0 µM was used to define specific binding. Incubation time was 60 minutes. All conditions were as described above. Data was analyzed by computer assisted non-linear regression (Accufit Saturation; Lundon Software; Chagrin Falls, Ohio).

Method for Binding Assays On a Stable Cell Line

Subsequent to analysis in transiently transfected cells, the 5-$HT_2$ clone was expressed as a stable transfectant in mouse $Ltk^-$ cells. Further characterization was done on these cells as described above. Specific binding was 75–85% of the total binding.

Competition studies for $^3$H-Ketanserin binding were performed by adding increasing concentrations of test drug to the reaction. 10–12 different concentrations of each ligand were tested and spanned the expected $IC_{50}$ range as determined from literature values. Data were analyzed by computer-assisted analysis (Accufit Competition; Lundon Software; Chagrin Falls, Ohio).

EXPERIMENTAL RESULTS

Nucleotide Sequence and Deduced Amino Acid Sequence of the Receptor Encoded by Clone 6B DNA sequence information obtained from clone 6B is shown in FIGS. 2A–2G. An opening frame extending from an ATG codon at position 1 to a stop codon at position 1414 can encode a protein 471 amino acids in length, having a relative molecular mass ($M_r$) of 52,542. A comparison of this protein sequence with previously characterized neurotransmitter receptors indicates that clone 6B is a new member of a family of molecules which span the lipid bilayer seven times and couple to guanine nucleotide regulatory proteins (the G protein-coupled receptor family). A variety of structural features which are invariant in this family were present in clone 6B. The greatest homology was found between clone 6B and the rat 5-$HT_{1C}$ and rat 5-$HT_2$ receptors. Overall, 90% sequence conservation between the rat and human 5-$HT_2$ clones was observed over 471 amino acids. There is considerable divergence between rat and human protein sequences at the extracellular amino and cytoplasmic carboxy termino. Only 76% of the residues are conserved in these regions. In contrast, between these regions, which included transmembrane region domains and transmembrane loops, 98% of the residues are conserved.

Receptor Expression in Transfected Mammalian Cells

In order to confirm the functional identity of the newly isolated gene we have expressed clone 6B in cultured cell lines. A DNA fragment containing the entire coding region was subcloned into the expression vector pMO5. The resulting plasmid pMO5-6B was transiently introduced into Cos-7 cells using the DEAE-dextran protocol (Cullen, Methods in Enz. 152: 684–704, 1987).

Stable cell lines were produced by cotransfection with the plasmid containing the bacterial gene aminoglycoside phosphtransferase into Ltk⁻ cells (American Type Culture Collection, Rockville, Md., Cell Line CCL 1,3) using the calcium phosphatase technique (Protocol & kit obtained from Specialty Media, Inc. Lavallette, N.J.). Clones expressing aminoglycoside transferase were selected for the addition 1 mg/ml G418 (Gibco Laboratories, Grand Island, N.Y.) to the culture medium. $^3$H-Ketanserin and $^3$H-DOB binding were used to monitor 5-HT$_2$ receptor gene expression in these clones. Three out of sixteen clones displayed specific binding of both $^3$H-Ketanserin and $^3$H-DOB. The remainder bound neither radioligand.

Cos-7 cells or Ltk⁻ cells were pseudotransfected with pMO5 not containing an insert in order to assess endogenous levels of ligand binding. At 1 nM or 2 nM radioligand, no significant specific binding was detected. The background was low [100 CPM for $^3$H-Ketanserin and 20 CPM for $^3$H-DOB] for both cell lines. Therefore, Cos-7 and Ltk⁻ cells provide useful models for transfection of a putative 5-HT$_2$ receptor. Transiently transfected Cos-7 cells bound $^3$H-Ketanserin with high affinity, and with an estimated site density of 0.95–1.6 pm/mg protein. These cells also bound $^3$H-DOB with high affinity and with a site density of 0.26–0.5 pm/mg protein. $^3$H-DOB binding constituted approximately 30% of the $^3$H-Ketanserin binding sites.

Full saturation analysis was performed on stable cell lines expressing the gene. Ltk⁻ cells transfected with pMO5-6B bound $^3$H-Ketanserin saturably, specifically, and with high affinity. The binding constants were evaluated by computer-assisted nonlinear regression using Accufit (Lundon Software, Chagrin Falls, Ohio). The equilibrium dissociation constant was 0.678±0.13 nM and the $B_{max}$=0.602±0.07 pm/mg protein (See FIG. 4). Further characterization was accomplished by performing competition experiments for a series of drugs. Analysis of the competition data was accomplished using the computer-assisted nonlinear regression program Accucomp. Data are shown in Table 1.

TABLE 1

PROPERTIES OF 3H-KETANSERIN BINDING TO THE CLONED HUMAN 5-HT2 RECEPTOR EXPRESSED IN LTK- CELLS.

| DRUG | $K_i$ (nM) HUMAN | n | $K_i$ (nM) HUMAN CORTEX | $K_i$ (nM) RAT CORTEX[2] |
|---|---|---|---|---|
| SPIPERONE | 0.22 ± .03 | 3 | 0.42[1] | 1.5 |
| 5-HT | 224.0 ± 22 | 4 | 174[2] | 79 |
| MESULERGINE | 146 ± 5 | 2 | 158[2] | 5 |
| RITANSERIN | 1.29 | 1 | 1.26[2] | 7.2 |
| CYPROHEPTADINE | 2.95 ± 0.10 | 2 | 6.3[2] | 1.8 |
| METHYSERGIDE | 2.62 ± 0.12 | 2 | 2.5[2] | 4 |
| BUTACLAMOL | 9.0 | 1 | 2.4[1] | — |
| 5-CT | 3032 | 1 | 813[2] | 19953 |

[1]Lyon, et al., Mol. Pharmacol. 31: 194–199 (1987).
[2]Hoyer, et al., brain Res. 376: 97–107 (1986).

The high affinity of pMO5-6B transfected Cos-7 or Ltk⁻ membranes for $^3$H-Ketanserin indicates that this clone can code for the production of 5-HT$_2$ binding site in its otherwise naive host cells.

Discussion

Applicants have cloned and characterized a cDNA molecule encoding an human 5-HT$_2$ receptor. The expression of this cDNA clone in Cos-7 cells and Ltk⁻ cells results in the appearance of this type of receptor on the cell surface.

Binding competition studies of pMO5-6B transfected Cos-7 or Ltk⁻ cell membranes with $^3$H-Ketanserin (Table 1) indicate that this clone is a 5-HT$_2$ receptor. Furthermore, the pharmacological profile of the cloned human receptor closely matches that of the $^3$H-Ketanserin binding to the 5-HT$_2$ receptor in human cortical membranes rather than in rat cortical membranes even though the human receptor was expressed (by transfection) in a mouse fibroblast cell line (Ltk⁻). This species difference is particularly evident for Mesulergine (see Table 1). This data strongly suggests that the species differences in pharmacological binding properties of the human 5-HT$_2$ receptor arise from amino acid differences in this protein rather than the cellular environment in which it is translated, processed and inserted in the cell membrane. Thus, the key parameter in obtaining a human-like pharmacology of the 5-HT$_2$ receptor appears to be the human gene sequence, rather than the cell type in which it is expressed. Therefore, isolation of the human gene provides the critical tool needed for the development of heterologous expression systems which will accurately model the pharmacological properties of human brain tissue. Moreover, the fact that these transfected cell membranes bind both $^3$H-Ketanserin and $^3$H-DOB demonstrates that the reported "hallucinogen receptor" must be an affinity state of the 5-HT$_2$ receptor rather than a distinct receptor subtype. This observation provides the opportunity to use the transfected human 5-HT$_2$ receptor as a tool for the development of drugs which induce or which interfere with hallucinogenesis, caused either by disease processes or by drugs of abuse.

What is claimed is:

1. An isolated nucleic acid molecule encoding a human 5-HT$_2$ receptor having the amino acid sequence as shown in FIGS. 2A–2G.
2. A DNA molecule of claim 1.
3. A vector comprising the DNA molecule of claim 2.
4. A virus comprising the DNA molecule of claim 2.
5. A bacteriophage comprising the DNA molecule of claim 2.
6. A plasmid comprising the DNA molecule of claim 2.
7. A mammalian cell comprising the plasmid of claim 6.
8. A cDNA molecule of claim 1.
9. A vector comprising the cDNA molecule of claim 8.
10. A virus comprising the cDNA molecule of claim 8.
11. A bacteriophage comprising the cDNA molecule of claim 8.
12. A plasmid comprising the cDNA molecule of claim 8.
13. The plasmid of claim 12 designated clone 6B.
14. A mammalian cell comprising the plasmid of claim 12.
15. The plasmid designated pMO5-6B.
16. A mammalian cell comprising the plasmid of claim 15.
17. A transfected Ltk– cell comprising the plasmid of claim 15.
18. The transfected Ltk– cell designated L-NGC-5HT$_2$.

* * * * *